(12) United States Patent
Khamar et al.

(10) Patent No.: US 9,345,683 B2
(45) Date of Patent: May 24, 2016

(54) PHARMACEUTICAL COMPOSITION OF TAXOIDS

(75) Inventors: Bakulesh Mafatlal Khamar, Ahmedabad (IN); Ashish Premkumar Gogia, Ahmedabad (IN); Ritu Nitin Laddha, Ahmedabad (IN); Imran Ahmed Khan, Ahmedabad (IN); Vandana Bharat Patravale, Ahmedabad (IN); Indravadan Ambalal Modi, Ahmedabad (IN)

(73) Assignee: Cadila Pharmaceuticals Limited, Ahmedabad (IN)

( * ) Notice: Subject to any disclaimer, the term of this patent is extended or adjusted under 35 U.S.C. 154(b) by 0 days.

(21) Appl. No.: 13/884,182

(22) PCT Filed: Nov. 5, 2011

(86) PCT No.: PCT/IB2011/054944
§ 371 (c)(1),
(2), (4) Date: Jul. 22, 2013

(87) PCT Pub. No.: WO2012/063182
PCT Pub. Date: May 18, 2012

(65) Prior Publication Data
US 2013/0310447 A1    Nov. 21, 2013

(30) Foreign Application Priority Data

Nov. 8, 2010    (IN) .................. 3068/MUM/2010

(51) Int. Cl.
| A61K 31/335 | (2006.01) |
| A01N 43/02 | (2006.01) |
| A61K 31/337 | (2006.01) |
| A61K 9/107 | (2006.01) |
| A61K 9/48 | (2006.01) |
| A61K 47/10 | (2006.01) |
| A61K 47/14 | (2006.01) |
| A61K 47/22 | (2006.01) |
| A61K 47/26 | (2006.01) |
| A61K 47/44 | (2006.01) |

(52) U.S. Cl.
CPC ............. *A61K 31/337* (2013.01); *A61K 9/1075* (2013.01); *A61K 9/4858* (2013.01); *A61K 47/10* (2013.01); *A61K 47/14* (2013.01); *A61K 47/22* (2013.01); *A61K 47/26* (2013.01); *A61K 47/44* (2013.01)

(58) Field of Classification Search
None
See application file for complete search history.

(56) References Cited

U.S. PATENT DOCUMENTS

| 6,046,230 | A | 4/2000 | Chung et al. | |
| 2003/0109575 | A1* | 6/2003 | Lambert et al. | ............... 514/458 |
| 2004/0092428 | A1 | 5/2004 | Chen et al. | |
| 2005/0026898 | A1 | 2/2005 | Peracchia et al. | |
| 2005/0191323 | A1 | 9/2005 | Chen | |
| 2006/0292186 | A1 | 12/2006 | Garrigue et al. | |
| 2007/0036834 | A1* | 2/2007 | Pauletti et al. | ............... 424/426 |
| 2009/0324703 | A1 | 12/2009 | Frautschy et al. | |

FOREIGN PATENT DOCUMENTS

EP    1480636 A2    12/2004

OTHER PUBLICATIONS

Gelderblom et al. (European Journal of Cancer, 2001, 37, 1590-1598).*
Tarr et al. (1987) Pharm. Res. 4:162-165.
Shicheng Yang et al., Pharmaceutical Research 21(2), 2004.
International Search Report dated Apr. 18, 2012 in corresponding International Patent Application No. PCT/IB2011/054944.

* cited by examiner

*Primary Examiner* — Dennis Heyer
*Assistant Examiner* — Daniel M Podgorski
(74) *Attorney, Agent, or Firm* — Pepper Hamilton LLP

(57) ABSTRACT

The present invention relates to a stable oral pharmaceutical composition with improved solubility and bioavailability; comprising a taxoid, a solubilizer, a stabilizing agent, a surfactant(s), a solvent(s), and an oil wherein the concentration of taxoid is in the range of 0.1 to 10%.

9 Claims, 1 Drawing Sheet

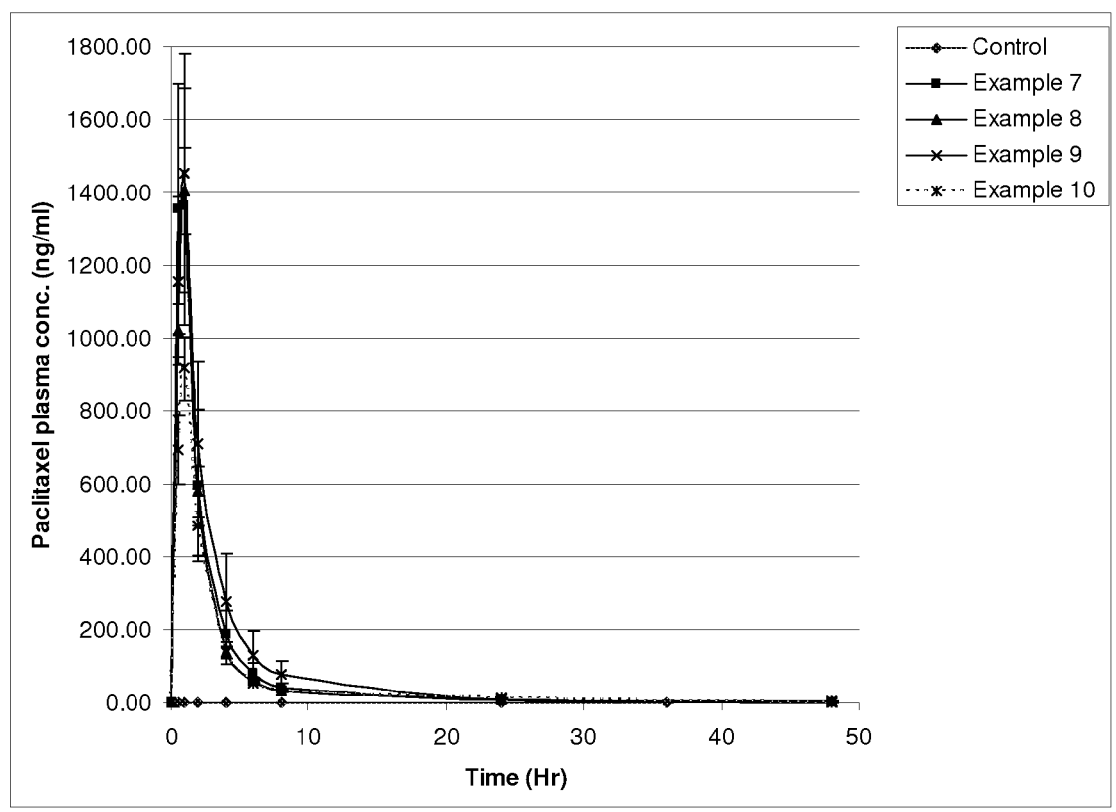

PHARMACEUTICAL COMPOSITION OF TAXOIDS

This application is a national phase filing under 35 U.S.C. §371 of International Patent Application No. PCT/IB2011/054944, filed Nov. 5, 2011, which claims the benefit of Indian Patent Application No. 3068/MUM/2010, filed Nov. 8, 2010, each of which is incorporated herein by reference in its entirety.

FIELD OF THE INVENTION

The present invention relates to a stable pharmaceutical composition of taxoids and process for preparing the same.

BACKGROUND OF THE INVENTION

Taxoids are a class of derivatives from taxol. These are antitumor agents which have been shown to be active against leukemia, colon cancer, breast cancer, melanoma, sarcomas, and lewis lung tumor systems. Taxoids are poorly water soluble and pose formulation related problems to prepare safe and stable pharmaceutical composition.

The commercially available I.V. taxoids formulation marketed by Bristol-Myers Squibb (Taxol®) comprises 6 mg/ml of paclitaxel dissolved in a mixture of 50:50 of Cremophor EL (polyoxyethylated castor oil) and dehydrated ethanol. The said composition has shown a loss of potency of greater than 60% after storage at 50° C. for 12 weeks which was attributed to the decomposition of paclitaxel during storage. In general, the amount of Cremophor EL necessary to deliver the required dose of paclitaxel is significantly higher than that administered with other drugs currently formulated in Cremophor EL. The use of Cremophor EL has been attributed to several toxic effects such as vasodilation, dyspnea and hypotension. Both poor oral absorption of paclitaxel molecule and parenteral toxicity of paclitaxel injection suggest the need of a high bio-available oral formulation of the same.

Tarr et al. (1987) Pharm. Res. 4:162-165, attempted to formulate taxol with Intralipid (trademark of RabiVitrum (formerly Cutter Medical)) and discloses the composition comprising soybean oil, lecithin, egg yolk phospholipids and glycerol. The poor solubility of taxol in soybean oil (0.3 mg/ml) made this vehicle unsuitable.

EP1480636 discloses a self emulsifying drug delivery system (SEEDS) of paclitaxel comprising vitamin E and a co-solvent selected from propylene glycol and ethanol, one or more bile salts like deoxycholic acid sodium salt (DOC-Na), tocopheryl polyethylene glycol 1000 succinate (TPGS) and tyloxapol. The composition according to the invention is suitable for intravascular or oral administration. The said patent further discloses that the physical stability of paclitaxel in microemulsion decrease with increasing concentration of paclitaxel in SEDDS composition. The animal pharmacokinetic study revealed that after intravenous administration of said formulation the $AUC_{0-\alpha}$ of paclitaxel was 4392.1 ng·hr/ml at the dose of 2 mg/kg and increased to 10129.9 and 72846.3 ng·hr/ml at the dose of 5 mg/kg and 10 mg/kg, respectively. Further, for oral administration, the SEDDS were diluted with water (in 1:10) and the values of $C_{max}$ were found between 40 to 60 ng/ml at the doses of 2 to 10 mg/kg. The said formulation was co-administered with cyclosporine A at dose of 40 mg/kg body weight that resulted in a $C_{max}$ of 85 ng/ml and 1.59 fold increase in bioavailability against SEEDS alone. The highest bioavailability of paclitaxel in oral administration was achieved at the dose of 5 mg/kg with 1.25% w/w concentration of paclitaxel. Said patent concluded that there is a decrease in AUC with increase in dose as well as paclitaxel concentration in formulation due to saturable process in the absorption of oral paclitaxel.

U.S. Pat. No. 6,046,230 discloses use of admixture of polyethoxylated sorbitol oleic polyester and polyethylene glycol mono fatty acid ester for preparation of improved paclitaxel injection and polyethylene glycol and polyvinyl pyrrolidone to achieve the quick dispersion of paclitaxel and stability of the formulation up to 5 days. The concentration of paclitaxel in stock solution was 0.6% and when stock solution was diluted at the ratio of 1:10 and 1:50 in 0.9% NaCl, the precipitation of paclitaxel occurred after 72 hours.

US20040092428A1 discloses ethanol and cremophor free oral formulation comprising of paclitaxel (83 to 100 mg/ml), and one or more of oil (triacetin), solvent (PEG 400, transcutol), surfactant (polysorbate 80) and organic acid (citric acid). An inhibitor of P-glycoprotein (cyclosporine A) is also administered before, during, or after the administration of paclitaxel formulation in order to improve the uptake of paclitaxel by gastrointestinal system. The said formulation resulted in maximum plasma concentration of 0.35 μg/ml.

US 20050191323 discloses preparation of stable cremophor-free formulation comprising paclitaxel (6 mg/ml), one or more solubilizer selected from PEG-Vitamin E, quaternary ammonium salts, PEG monoacid fatty esters, PEG-glyceryl fatty esters, polysorbates, PEG-fatty alcohols. Paclitaxel formulation disclosed by present application contains stabilizer like citric acid to prevent the decomposition of paclitaxel and maintain the pH of composition. The paclitaxel concentration in composition was 1.2 mg/ml and stayed dissolved only for 48 hours. Animal pK study revealed that bioavailability of the formulation is lower than the commercially available formulation.

US20060292186A1 discloses oral anhydrous self-nanoemulsifying oily formulation (SNEOF) comprising paclitaxel (1.5 to 3.0% w/w), vitamin E, co-solvent selected from propylene glycol and ethanol or mixture thereof and surfactant selected from tyloxapol and TPGS or mixture thereof and optionally a bioenhancer (cyclosporine A). However, there was no significant improvement in bioavailability of the same formulation when administered in wild type mice.

Most of the above reports make use of cyclosporine A which is an immunosuppressive agent and hence is undesirable in the formulation.

Oral pharmaceutical compositions of paclitaxel with lower/poor bioavailability are associated with diarrhea.

Despite several attempts by many researchers, there is an unmet need to develop a pharmaceutical composition of taxoids which provides therapeutic level of taxoids in serum and said composition also improves the stability, solubility and bioavailability of taxoids.

The term "therapeutic level of taxoid in serum' as used herein is referred to minimum effective concentration of taxoid in serum. As per the present invention "therapeutic level of taxoid in serum" should be at least 85.3 ng/ml (shicheng yang et al. pharmaceutical research 21(2), 2004).

The term "stable" as used herein is related to physical and/or chemical stability. In physical stability, the drug should not be crystallized or precipitated in the pharmaceutical composition during shelf life or stability conditions for at least three months. In chemical stability as per the international conference on harmonization (ICH) guidelines the active pharmaceutical ingredient should retain its 90% activity during the accelerated stability study for 3 months.

OBJECTS OF THE INVENTION

The object of the present invention is to provide a stable pharmaceutical composition of taxoids with improved solubility which prevents the precipitation of taxoids during the shelf life and process for preparing the same.

Another object of the present invention is to provide a stable pharmaceutical composition suitable for oral administration with higher concentration of taxoids.

Yet another object of the present invention is to provide a stable pharmaceutical composition with improved bioavailability in mammal when administered orally.

Yet another object of the present invention is to provide a stable pharmaceutical composition which provides therapeutic level of taxoids in serum of mammal when administered orally.

DETAILED DESCRIPTION OF THE DRAWING

FIG. 1 represents comparative pharmacokinetic profiles of different pharmaceutical compositions of paclitaxel in rats (n=6).

DETAILED DESCRIPTION OF THE INVENTION

Accordingly, the pharmaceutical composition comprises of taxoids, solubilizer, stabilizing agent, surfactant(s), solvent (s) and oil wherein the ratio of solubilizer to taxoid and stabilizing agent to taxoid are in the range of 3 to 150 and 0.5 to 3.3, respectively. The therapeutic level of taxoids in the serum is more than 85 ng/ml.

The invention provides a stable self emulsifying composition with improved solubility and bioavailability wherein the amount of taxoids is 0.1 to 10% w/w, preferably 0.4 to 6% w/w.

Taxoid is selected from Paclitaxel or Docetaxel or a derivative or a pharmaceutically acceptable salt thereof.

Surfactant is selected from capryl/caproyl macrogel glycerides (Labrasol®), alpha-tochopherol polyethylene glycol 1000 succinate, polysorbate and PEG hydrogenated castor oil. The concentration of the surfactant in the composition ranges from 10 to 60% w/w.

Solvent is selected from propylene glycol and alcohol. The concentration of the solvent in the composition ranges from 5 to 25% w/w.

Oil is selected from: (1) medium chain fatty acid triglycerides such as fractionated coconut oil, Caprylic/capric triglyceride, (2) esters of fatty acids and monovalent alkanols such as isopropyl myristate, isopropyl palmitate, ethyl linoleate and ethyl oleate and (3) propyleneglycol di-fatty acid esters such as propyleneglycol dicaprylate, propyleneglycol dilaurate. The concentration of the oil in the composition ranges from 30 to 80% w/w.

The solubilizer is selected from diethylene glycol monoethyl ether (Transcutol HP) and glycofurol. The concentration of the solubilizer in the composition ranges from 15 to 30% w/w.

The stabilizing agent is selected from piperine, polyvinyl caprolactam-polyvinyl acetate-polyethylene glycol graft copolymer (Soluplus), polyvinyl pyrrilidone, and hydroxypropyl methyl cellulose, preferably piperine. The concentration of stabilizing agent in the composition ranges from 1 to 7.5% w/w.

The stable pharmaceutical composition of taxoids as per the invention is administered to mammal by oral route.

The present invention also provides a process for preparing the stable oral self emulsifying pharmaceutical composition with improved solubility and bioavailability comprising:
i). Dissolving taxoid in solvent;
ii). Adding solubilizer and surfactant(s) to the composition of step i) with continuous stirring;
iii). Adding and dissolving the stabilizing agent in composition of step ii) and adding oil under continuous stirring till desired weight is achieved.

In one embodiment a process for the preparation of the said composition comprising:
i). Dissolving taxoid in solubilizer;
ii). Adding surfactant(s) to the composition of step i) with continuous stirring;
iii). Adding solvent to the composition of step ii) with continuous stirring;
iv). Adding and dissolving the stabilizing agent in composition of step iii) and
v). Adding oil under continuous stirring till desired weight is achieved.

Though pharmaceutical compositions prepared without stabilizing agent are stable, they loose their physical characteristics on dilution prior to administration. The stabilized composition has a particle size less than 500 nm. The bioavailability of stabilized compositions is significantly higher than those without stabilizing agent.

The invention is illustrated by the following examples which are only meant to illustrate the invention and not act as limitations.

EXAMPLES

A: Pharmaceutical Compositions

I): Pharmaceutical Compositions without Stabilizing Agent

Example 1

Pharmaceutical Composition

A pharmaceutical composition as disclosed in table 1 was prepared using following process.
i). Dissolving paclitaxel in ethanol;
ii). Adding Cremophore RH 40 and Vitamin E TPGS to the step i) with continuous stirring;
iii). Adding propylene glycol to step ii) with continuous stirring; and
iv). Adding crodamol GTCC till 30 g weight of composition is achieved.

TABLE 1

| Composition for example 1 | | |
|---|---|---|
| S. No. | Ingredients | Qty/30 g |
| 1. | Paclitaxel | 0.180 g |
| 2. | Cremophor RH40 (Polyoxyl 40 Hydrogenated Castor Oil) | 3.00 g |
| 3. | Vitamin E TPGS (D-alpha-tocopheryl polyethylene glycol 1000 succinate) | 6.00 g |
| 5. | Ethanol | 3.00 g |
| 4. | Propylene glycol | 3.00 g |
| 6. | Crodamol GTCC (Caprylic Capric Triglyceride) QS | 30.00 g |

Example 2

Pharmaceutical Composition

A pharmaceutical composition as disclosed in table 2 was prepared using following process.

i). Dissolving paclitaxel in Transcutol HP;
ii). Adding Cremophore RH 40, Labrasol and Vitamin E TPGS to the step i) with continuous stirring;
iii). Adding propylene glycol to step ii) with continuous stirring; and
iv). Adding labrafil till 100 g weight of composition is achieved.

TABLE 2

Composition for Example 2

| S. No. | Ingredients | Quantity 100 g |
|---|---|---|
| 1 | Paclitaxel | 2.0 g |
| 2 | Cremophor RH40 | 10.0 g |
| 3 | Vitamin E TPGS | 10.0 g |
| 4 | Propylene glycol | 10.0 g |
| 5 | Labrasol | 25.0 g |
| 6 | Transcutol HP | 25.0 g |
| 7 | Labrafil QS | 100.0 g |

Example 3

Pharmaceutical Composition

A pharmaceutical composition as disclosed in table 3 was prepared using following process.
i). Dissolving paclitaxel in mixture of ethanol and Trancutol HP;
ii). Adding Cremophore RH 40, Labrasol and Vitamin E TPGS to the step i) with continuous stirring;
iii). Adding propylene glycol to step ii) with continuous stirring; and
iv). Adding labrafil till 100 g weight of composition is achieved.

TABLE 3

Composition for Example 3

| Sr. No | Ingredient | Quantity 100 g |
|---|---|---|
| 1 | Paclitaxel | 4.0 g |
| 2 | Cremophor RH40 | 10.0 gm |
| 3 | Vitamin E TPGS | 10.0 gm |
| 4 | Alcohol | 10.0 gm |
| 5 | Propylene glycol | 10.0 gm |
| 6 | Labrasol | 20.0 gm |
| 7 | Transcutol HP | 20.0 gm |
| 8 | Labrafil QS | 100.0 gm |

Pharmaceutical composition without stabilizing agent were found to be stable but resulted in altered physical characteristics on dilution with water.

II): Pharmaceutical Compositions with Stabilizing Agent

Example 4

Pharmaceutical Composition

A pharmaceutical composition as disclosed in table 4 was prepared using following process.
i). Dissolving paclitaxel in ethanol;
ii). Adding Cremophor RH 40 and Vitamin E TPGS to the step i) with continuous stirring;
iii). Adding propylene glycol to step ii) with continuous stirring;
iv). Piperine was added to resulting composition of step iii) and dissolved under stirring; and
v). Adding crodamol GTCC till 1 g weight of composition is achieved.

TABLE 4

Composition for example 4

| S. No. | Ingredients | 1 gm |
|---|---|---|
| 1. | Paclitaxel | 6 mg |
| 2. | Piperine | 20 mg |
| 3. | Cremophor RH40 (Polyoxyl 40 Hydrogenated Castor Oil) | 100 mg |
| 4. | Vitamin E TPGS (D-alpha-tocopheryl polyethylene glycol 1000 succinate) | 200 mg |
| 5. | Ethanol | 100 mg |
| 6. | Propylene glycol | 100 mg |
| 7. | Crodamol GTCC (Caprylic Capric Triglyceride) QS | 500 mg |

Example 5

Pharmaceutical Composition

A pharmaceutical composition as disclosed in table 5 was prepared using following process.
i). Dissolving paclitaxel in mixture of ethanol and Trancutol HP;
ii). Adding Cremophor RH 40 and Vitamin E TPGS to the step i) with continuous stirring;
iii). Adding propylene glycol, Labrasol, to step ii) with continuous stirring;
iv). Piperine was added to resulting composition of step iii) and dissolved under stirring; and
v). Adding labrafil till 1 g weight of composition is achieved.

TABLE 5

Composition for example 5

| S. No. | Ingredients | 1 gm |
|---|---|---|
| 1 | Paclitaxel | 40 mg |
| 2 | Piperine | 20 mg |
| 3 | Cremophor RH40 (Polyoxyl 40 Hydrogenated Castor Oil) | 100 mg |
| 4 | Vitamin E TPGS (D-alpha-tocopheryl polyethylene glycol 1000 succinate) | 100 mg |
| 5 | Ethanol | 100 mg |
| 6 | Propylene glycol | 100 mg |
| 7 | Labrasol | 200 mg |
| 8 | Labrafil | 200 mg |
| 9 | Transcutol HP | 200 mg |

Example 6

Pharmaceutical Composition

A pharmaceutical composition as disclosed in table 6 was prepared using following process.
i). Dissolving paclitaxel in mixture of ethanol and Trancutol HP;

ii). Adding Cremophor RH 40 and Vitamin E TPGS to the step i) with continuous stirring;
iii). Adding propylene glycol, Labrasol, and Labrafil. to step ii) with continuous stirring;
iv). Piperine was added to resulting composition of step III) and dissolved under stirring; and
v). Adding labrafil till 1 g weight of composition is achieved.

TABLE 6

Composition for example 6

| S. No. | Ingredients | 1 gm |
|---|---|---|
| 1 | Paclitaxel | 20 mg |
| 2 | Piperine | 15 mg |
| 3 | Cremophor RH40 (Polyoxyl 40 Hydrogenated Castor Oil) | 100 mg |
| 4 | Vitamin E TPGS (D-alpha-tocopheryl polyethylene glycol 1000 succinate) | 100 mg |
| 6 | Propylene glycol | 100 mg |
| 7 | Labrasol | 239.8 mg |
| 8 | Labrafil | 200 mg |
| 9 | Transcutol HP | 239.8 mg |

Example 7-10

Pharmaceutical Composition

The pharmaceutical compositions as disclosed in table 7 were prepared using following process.
i). Dissolving paclitaxel in mixture of ethanol and Trancutol HP;
ii). Adding Cremophor RH 40 and Vitamin E TPGS to the step i) with continuous stirring;
iii). Add propylene glycol, Labrasol, and Labrafil to step ii) with continuous stirring;
iv). Piperine was added to resulting composition of step iii) and dissolved under stirring; and
v). Adding labrafil till 1 g weight of composition is achieved.

TABLE 7

Compositions for examples 7-10

| S. No. | Ingredients | Example 7 (1 g) | Example 8 (1 g) | Example 9 (1 g) | Example 10 (1 g) |
|---|---|---|---|---|---|
| 1 | Paclitaxel | 40 mg | 50 mg | 60 mg | 70 mg |
| 2 | Piperine | 30 mg | 37.5 mg | 45 mg | 52 mg |
| 3 | Cremophor RH40 (Polyoxyl 40 Hydrogenated Castor Oil) | 100 mg | 100 mg | 100 mg | 100 mg |
| 4 | Vitamin E TPGS (D-alpha-tocopheryl polyethylene glycol 1000 succinate) | 100 mg | 100 mg | 100 mg | 100 mg |
| 5 | Ethanol | 100 mg | 100 mg | 100 mg | 100 mg |
| 6 | Propylene glycol | 80.92 mg | 63.4 mg | 45.9 mg | 28.9 mg |
| 7 | Labrasol | 179.6 mg | 179.6 mg | 179.6 mg | 179.6 mg |
| 8 | Labrafil | 189.8 mg | 189.8 mg | 189.8 mg | 189.8 mg |
| 9 | Transcutol HP | 179.6 mg | 179.6 mg | 179.6 mg | 179.6 mg |

Example 11

Pharmaceutical Composition

The pharmaceutical composition of example 11 as disclosed in table 8 was prepared using following process.
i). Dissolve docetaxel in mixture of ethanol and Trancutol HP and polysorbate 80;
ii). Add propylene glycol and Labrasol to step i) with continuous stirring;
iii). Add piperine to resulting composition of step ii) and dissolve under stirring; and
iv). Make up the weight to 1 gm with Labrafil.

TABLE 8

Composition for example 11

| Ingredients | Example 11 (Qty. mg) |
|---|---|
| Docetaxel | 40 mg |
| Piperine | 20 mg |
| Ethanol | 300 mg |
| Propylene glycol | 303.6 mg |
| Polysorbate 80 | 1027 mg |
| Labrasol | 201.2 mg |
| Labrafil | 569.4 mg |
| Transcutol HP | 538.8 mg |

Pharmaceutical compositions with stabilizing agent were found to be stable without change in physical characteristics even when diluted with water.

B: Pharmacokinetic Evaluation of Pharmaceutical Compositions

Pharmacokinetic study was performed in rats (n=6 for each group) of either sex weighing of approx 200 gm. Animals received paclitaxel in 0.2% sodium carboxymethyl cellulose aqueous solution (control sample) and pharmaceutical compositions as per examples 7 to 10. Animals of each group were dosed with paclitaxel at 24 mg/kg body weight.

The comparative plasma profile and pharmacokinetic parameters achieved by control and compositions disclosed in the invention are shown in FIG. 1 and Table 9, respectively. The data show significant improvement in bioavailability of the taxoids following oral administration in a mammal in comparison to control sample.

TABLE 9

Pharmacokinetic parameters of different compositions in rats

| Pharmacokinetic Parameter | Control | Example 7 | Example 8 | Example 9 | Example 10 |
|---|---|---|---|---|---|
| Cmax ng/ml | 0.707 | 1362.042 | 1403.903 | 1452.485 | 917.7448 |
| Tmax Hr | 8.50 | 1.00 | 1.00 | 1.00 | 1.00 |
| $AUC_{0-\infty}$ ng/ml · Hr | 9.43 | 3658.51 | 3371.63 | 4464.44 | 2676.71 |

Pharmaceutical compositions prepared as per present invention are found to be stable. The compositions without stabilizing agent though found to be stable looses its physical characteristics when diluted prior to administration to a mammal and results in decreased bioavailability. The bioavailability of composition without stabilizing agents is 30% or less compared to the identical composition with stabilizing agents. The compositions with stabilizing agent remain stable even when diluted for administration.

What is claimed is:

1. A stable oral pharmaceutical composition of taxoid with improved solubility and bioavailability for administration to a mammal, the composition comprising:
- a taxoid selected from Paclitaxel or Docetaxel or a pharmaceutically acceptable salt thereof;
- a solubilizer selected from diethylene glycol monoethyl ether, glycofurol, and polyoxyl 40 hydrogenated castor oil;
- a stabilizing agent selected from piperine, polyvinyl caprolactam-polyvinyl acetate-polyethylene glycol graft copolymer, polyvinyl pyrrolidone and hydroxypropyl methyl cellulose;
- a surfactant selected from capryl/caproyl macrogel glycerides, alpha-tochopherol polyethylene glycol 1000 succinate, polysorbate and PEG hydrogenated castor oil, and combinations thereof;
- a solvent selected from propylene glycol and ethyl alcohol, and combinations thereof; and
- an oil selected from: (1) medium chain fatty acid triglycerides selected from fractionated coconut oil, caprylic/capric triglyceride, (2) esters of fatty acids and monovalent alkanols selected from isopropyl myristate, isopropyl palmitate, ethyl linoleate and ethyl oleate and (3) propyleneglycol di-fatty acid esters selected from propyleneglycol dicaprylate, propyleneglycol dilaurate;
- wherein the ratio of solubilizer to taxoid and stabilizing agent to taxoid are in the range of 2.5 to 12.5 and 0.5 to 3.3, respectively.

2. The stable oral pharmaceutical composition as claimed in claim 1, wherein the concentration of taxoid is in the range of 0.1 to 10% w/w.

3. The stable oral pharmaceutical composition as claimed in claim 1, wherein the concentration of taxoid is preferably in the range of 0.4 to 6% w/w.

4. The stable oral pharmaceutical composition as claimed in claim 1, wherein concentration of surfactant is in the range of 10 to 60% w/w.

5. The stable oral pharmaceutical composition as claimed in claim 1, wherein concentration of solvent is in the range of 5 to 25% w/w.

6. The stable oral pharmaceutical composition as claimed in claim 1, wherein concentration of oil is in the range of 30 to 80% w/w.

7. The stable oral pharmaceutical composition as claimed in claim 1, wherein concentration of solubilizer is in the range of 15 to 30% w/w.

8. The stable oral pharmaceutical composition as claimed in claim 1, wherein stabilizer is piperine.

9. The stable oral pharmaceutical composition as claimed in claim 1, wherein the concentration of stabilizer is in the range of 1 to 7.5% w/w.

* * * * *